United States Patent
Bax

(10) Patent No.: US 8,264,105 B2
(45) Date of Patent: *Sep. 11, 2012

(54) RESONANT ACTUATOR FOR A PERSONAL CARE APPLIANCE HAVING A PROGRAMMABLE ACTUATION CAPABILITY

(75) Inventor: Pieter Johannes Bax, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/966,008

(22) Filed: Dec. 13, 2010

(65) Prior Publication Data

US 2011/0080061 A1      Apr. 7, 2011

Related U.S. Application Data

(63) Continuation of application No. 12/064,048, filed as application No. PCT/IB2006/052832 on Aug. 16, 2006, now Pat. No. 7,876,003.

(60) Provisional application No. 60/708,693, filed on Aug. 16, 2005.

(51) Int. Cl.
    *H02K 33/00*         (2006.01)
(52) U.S. Cl. ......... 310/36; 310/12.01; 310/15; 15/21.01
(58) Field of Classification Search ............... 310/12.01, 310/13, 15, 36, 27; 15/22.01–22.05, 21.01
    See application file for complete search history.

(56) References Cited

U.S. PATENT DOCUMENTS

| | | | |
|---|---|---|---|
| 5,231,336 A | 7/1993 | Van Namen | |
| 5,719,451 A | 2/1998 | Cook et al. | |
| 5,811,902 A | 9/1998 | Sato | |
| 5,959,381 A | 9/1999 | Fischer et al. | |
| 6,300,739 B1 | 10/2001 | Ratliff et al. | |
| 6,611,074 B2 * | 8/2003 | Bartolotti | 310/114 |

(Continued)

FOREIGN PATENT DOCUMENTS

EP          1193844         6/2001

(Continued)

OTHER PUBLICATIONS

Dr. Andrzej M. Pawlak: "Magnets in Modern Rotary Actuators", Industry Applications Conf., 1995 IEEE, 1995, vol. 1, pp. 498-504.

*Primary Examiner* — Quyen Leung
*Assistant Examiner* — Leda Pham

(57) ABSTRACT

The drive system for a personal care appliance, such as a toothbrush, includes a first opposing pair of permanent magnet assemblies positioned longitudinally along the length of the internal surface of a cylindrical appliance housing, each first permanent magnet assembly having one portion with a north polarity and the other portion a south polarity, and a second pair of permanent magnet assemblies which are orthogonal to the first pair of permanent magnet assemblies, one second permanent magnet assembly having a plurality of abutting first parts along the length thereof, the parts alternating between a north polarity and a south polarity, the other second permanent magnet assembly having similar parts with reversed polarity. First and second armatures are mounted on, or a portion thereof forms, a spindle element which extends along the length of and outward from the cylindrical housing. A plurality of drive windings are positioned around the armatures in such a manner that application of current to the windings, under programmable control, produces axial and/or tangential movement of the spindle and the workpiece.

7 Claims, 7 Drawing Sheets

U.S. PATENT DOCUMENTS

| | | |
|---|---|---|
| 6,700,230 B1 | 3/2004 | Gokturk |
| 6,774,588 B2 | 8/2004 | Ibuki |
| 6,849,970 B2 * | 2/2005 | Watanabe .................. 310/12.22 |
| 6,958,553 B2 | 10/2005 | Ichii et al. |
| 7,075,196 B1 | 7/2006 | Labriola, II |
| 7,218,018 B2 | 5/2007 | Hasegawa et al. |
| 7,317,273 B2 | 1/2008 | Yanagisawa |
| 7,328,474 B2 | 2/2008 | Nishinaka et al. |
| 7,382,067 B2 | 6/2008 | Nakagawa et al. |
| 7,449,810 B2 | 11/2008 | Yokota et al. |
| 7,476,990 B2 | 1/2009 | Nakagawa et al. |
| 7,538,460 B2 | 5/2009 | Labriola, II |
| 7,594,239 B2 | 9/2009 | Chang et al. |
| 7,661,653 B2 | 2/2010 | Kondoh |
| 7,876,003 B2 * | 1/2011 | Bax ................................ 310/36 |
| 2001/0043016 A1 | 11/2001 | Sung |
| 2004/0128781 A1 | 7/2004 | Kunita |
| 2005/0046282 A1 * | 3/2005 | Tang et al. ...................... 310/12 |

FOREIGN PATENT DOCUMENTS

| | | |
|---|---|---|
| EP | 1329203 | 1/2003 |
| EP | 1432106 A1 | 6/2004 |
| JP | 20044254410 | 2/2003 |
| WO | 04001948 | 12/2003 |
| WO | 2004047670 | 6/2004 |
| WO | 2004049547 | 6/2004 |
| WO | 2005006538 | 1/2005 |
| WO | 2005062445 | 7/2005 |
| WO | 2007020599 A2 | 2/2007 |
| WO | 2008105393 A1 | 9/2008 |

* cited by examiner

RESONANT ACTUATOR FOR A PERSONAL CARE APPLIANCE HAVING A PROGRAMMABLE ACTUATION CAPABILITY This application is a Continuation of and claims priority to under 35 USC 120 to U.S. patent application Ser. No. 12/064, 048, now U.S. Pat. No. 7,876,003 filed on Jul. 10, 2008 which claims priority to and is a 371 US National Stage Entry of PCT/IB06/52832, filed on Aug. 16, 2006 which in turn claims priority to U.S. Provisional Application Patent Serial No. 60/708,693, filed Aug. 16, 2005.

This invention relates generally to drive systems for a personal care appliance, such as a power toothbrush, and more specifically concerns a combined tangential/axial motion drive system having a programmable drive control capability.

There are many known actuation systems for power toothbrushes, or other personal care appliances, which drive an output shaft or other member on which a workpiece, such as a brushhead for a toothbrush, is mounted. Such actuators include motors, as well as magnetic and electromagnetic systems, having a wide variety of configurations and embodying numerous technical and structural concepts. However, such devices are typically capable of actuating the workpiece in only one mode, e.g. a rotational mode, which might typically be the case for a DC motor actuator. A single mode of motion can be limiting, particularly when different motions are suitable for different cleaning functions, including, for instance, cleaning different regions of the mouth, such as the teeth and the gums. Further, a single mode of motion typically includes a simple movement as opposed to complex patterns, such as for instance a figure eight motion. Even if a particular motion is complex, usually the appliance is limited to that one operating motion/mode.

It would be desirable to be able to select more than one mode of movement of the workpiece, particularly both simple and complex motions, as well as varying the complex motion, in order to accomplish various cleaning goals, even in the case of a power toothbrush.

Accordingly, the present is a drive system for a personal care appliance, comprising: a housing; a first opposing pair of stationary permanent magnet assemblies; a second opposing pair of stationary permanent magnet assemblies, approximately orthogonal to the first pair of permanent magnets; a shaft member mounted within the housing and capable of moving rotationally and longitudinally; a first armature assembly attached to or forming a part of the shaft member for moving the shaft member rotationally in cooperation with the first pair of stationary permanent magnets when energized; a second armature assembly attached to or forming a part of the shaft member for moving the shaft member longitudinally in cooperation with the second pair of stationary permanent magnets when energized; and a source of power and control assembly for selectively energizing the first and/or second armature assemblies to produce movement of the shaft and corresponding movement of a workpiece connected to, or part of, an assembly connected to the shaft.

Figure 1:
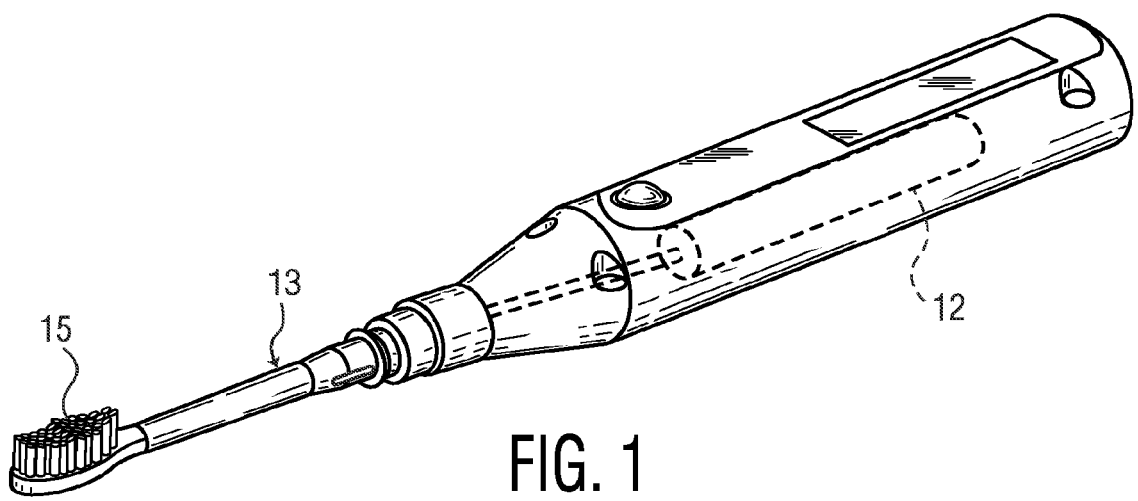
FIG. 1 is a simplified view of a power toothbrush.
Figure 2A:
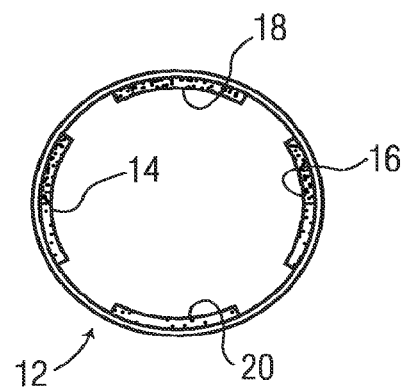
FIGS. 2A, 2B and 2C are various views of a portion of a first embodiment of the present invention.
Figure 2B:
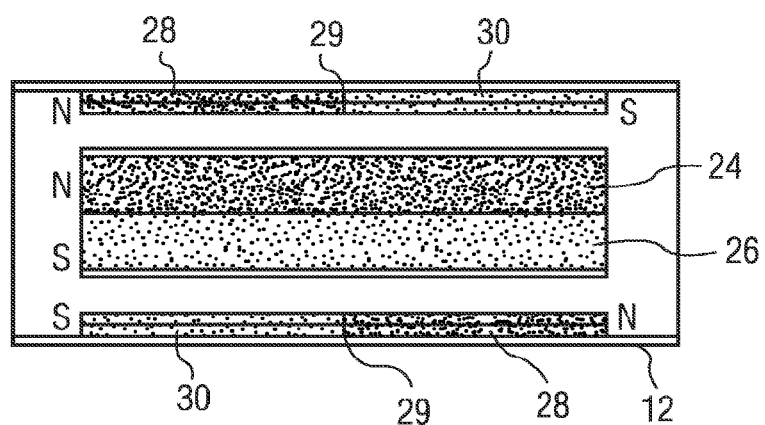
Figure 2C:
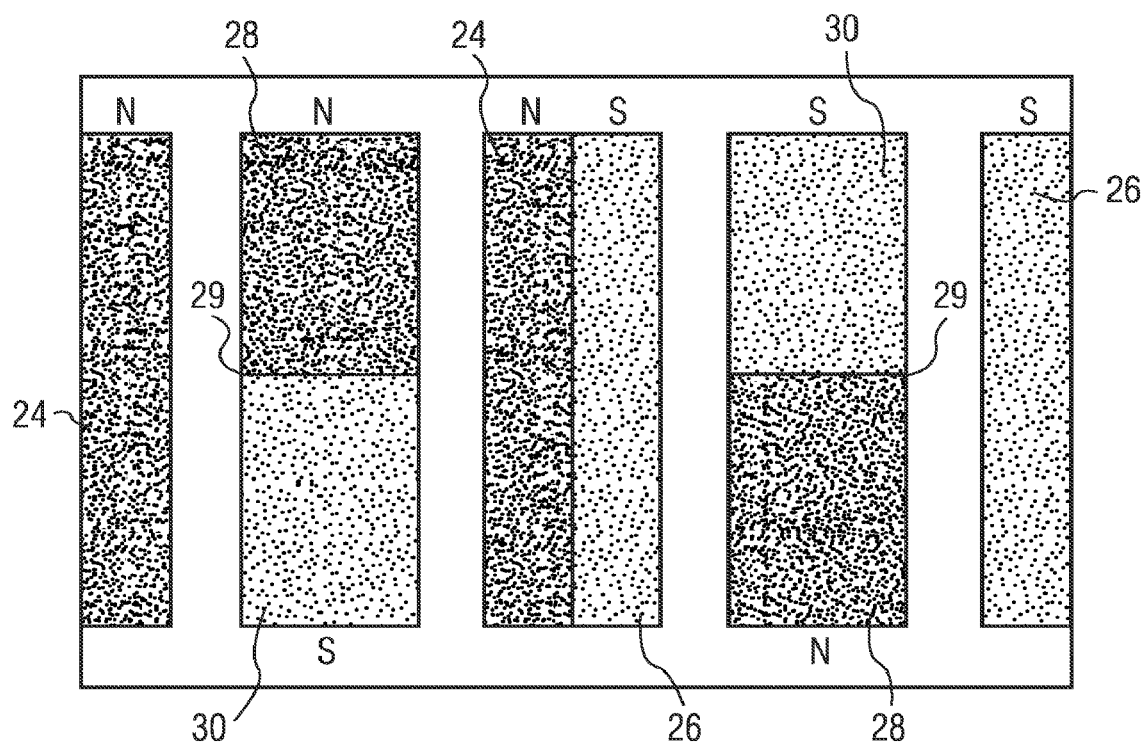

FIGS. 1, 2A-2C and 3A-3B show a first embodiment of a drive system (actuator) for a personal care appliance. The actuator embodiment includes a single cylindrical housing 12, with an actuator using magnetic action, mounted inside the housing. The actuator drives an output mounting shaft 13 on which is mounted a workpiece, such as a toothbrush 15. This embodiment includes four permanent magnet assemblies 14, 16, 18 and 20 positioned at 90° intervals around the interior of the cylindrical housing. Each permanent magnet assembly extends approximately the length of the housing 12, with a small space at both ends. In the embodiment shown, the cylindrical housing 12 can vary in diameter and length. Each permanent magnet assembly covers approximately 60°, although this can also be varied. The permanent magnets are curved to fit against the interior surface 13 of the housing 12. They can be attached to the housing by various means.

The permanent magnet assemblies 14, 16 each include two portions 24 and 26. Portion 24 has a north (N) polarity, while the other portion 26 has a south (S) polarity. Portions 24 and 26 each extend for the full length of magnet assemblies 14 and 16, but are reversed between portions 14 and 16, as shown most clearly in FIGS. 2B and 2C. Permanent magnet assemblies 18 and 20, as indicated above, are mounted in an opposing arrangement, orthogonal to magnets 14 and 16. Magnet assemblies 18 and 20 also each include two portions. One portion 28, which extends for the entire width of the magnet, from one longitudinal end thereof to approximately the mid-point 29 thereof, has a north (N) polarity, while the other portion 30, which extends from mid-point 29 (abutting portion 28) to the other longitudinal end, has a south (S) polarity. The portions 28 and 30 are reversed between magnet assemblies 18 and 20, again as shown most clearly in FIGS. 2B and 2C.

Figure 3A:
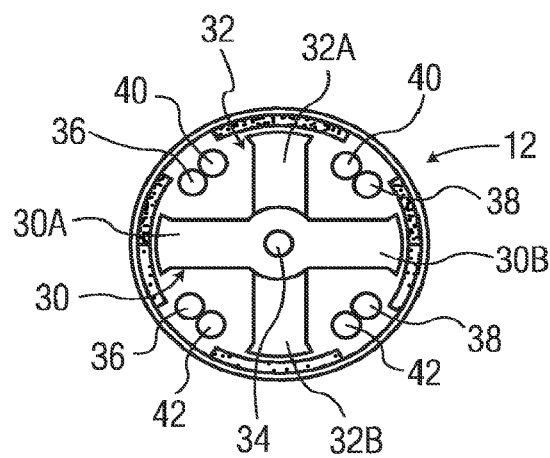
FIGS. 3A and 3B are lateral and longitudinal cross-sectional views of the embodiment of FIGS. 2A-2C, showing the moving armatures and the associated coil windings.
Figure 3B:
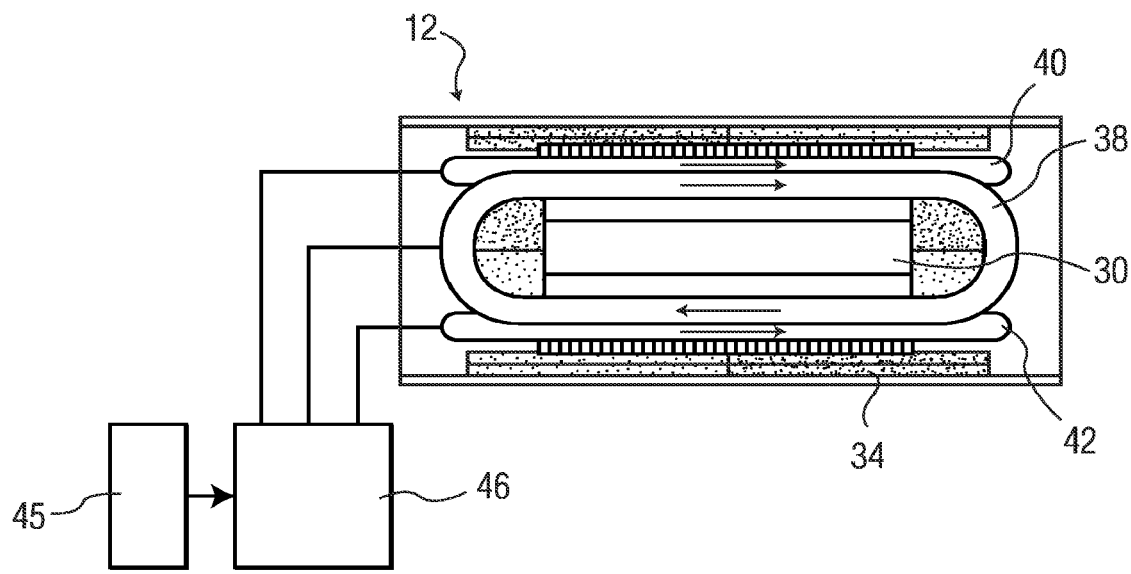
Figure 4A:
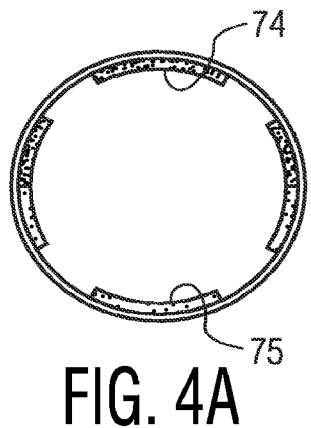
FIGS. 4A, 4B and 4C are various views of a portion of an alternative embodiment to the structure of FIGS. 2A-2C.
Figure 4B:
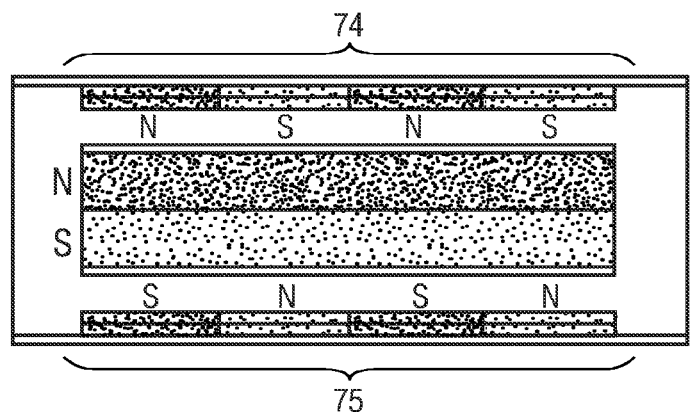
Figure 4C:
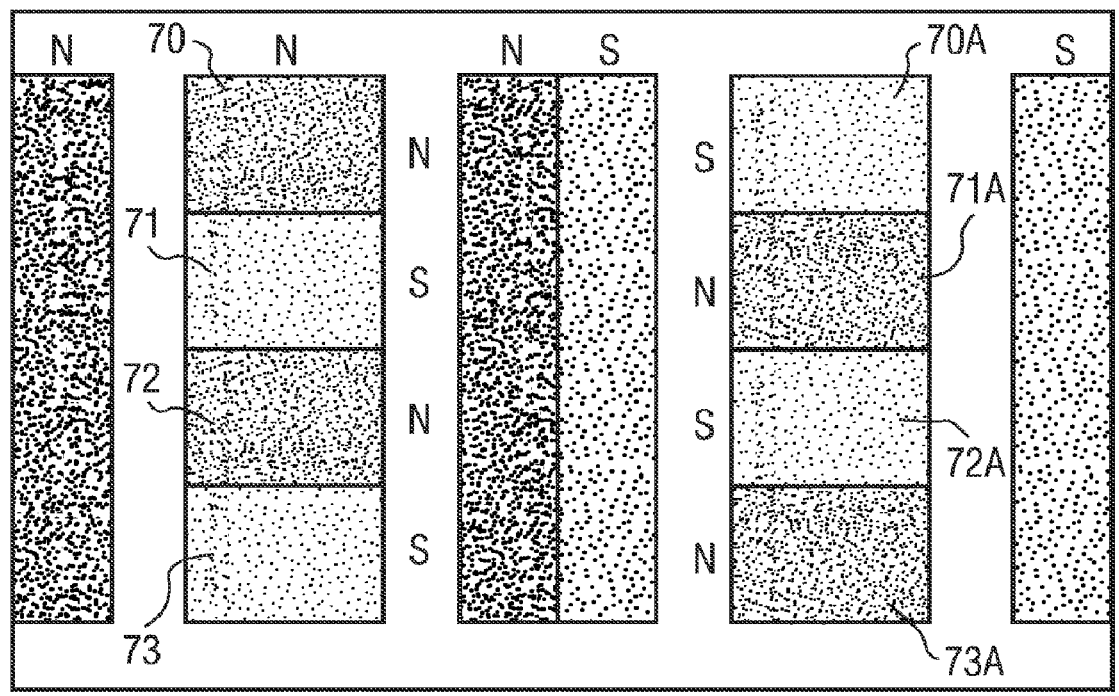

FIGS. 3A and 3B include a tangentially (rotationally) moving actuator/armature member 30 and an axially moving actuator/armature member 32. Tangential actuator 30 is connected to and in operation rotates spindle 34 which is mounted along the center of the cylindrical housing 12. The workpiece is mounted to the end of the spindle, which extends out of housing 12. Axial actuator 32, also connected to spindle 34, in operation moves the spindle axially. In one embodiment, actuators 30 and are combined with spindle 34, resulting in a single, integrated member.

Providing tangential (rotational) movement to the spindle and the workpiece are two windings 36 and 38 positioned around opposing parts 30A, 30B of tangential actuator 30, while windings 40 and 42 are positioned around opposing parts 32A, 32B of axial actuator 32, as shown in FIGS. 3A and 3B. Windings 40 and 42 are arranged and mounted (they do not move) so as to provide sufficient room for the actuator system and the spindle to move axially.

Power is provided to various windings by a conventional power supply, such as a battery 45, which typically is rechargeable.

A programmable control unit 46 controls the application of current to the various windings. The frequency and magnitude can be varied to provide selected complex movement of the workpiece, such as a movement in addition to just axial or just tangential (rotational) movement alone.

It should be understood that the physical arrangement of the permanent magnet assemblies and the actuator elements can be varied. For instance, the width of the axial actuator element 32 can be increased at its free ends to the full width of the permanent magnet assemblies, to provide more powerful actuation.

Figure 5A:
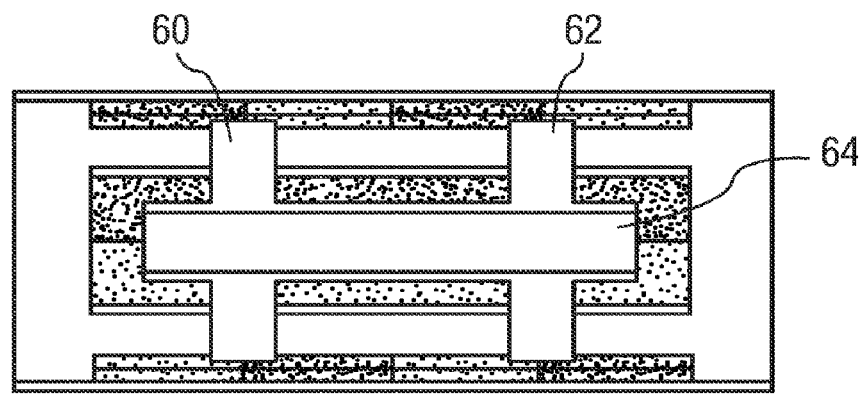
FIGS. 5A-5C are lateral and longitudinal cross-sectional views of the embodiment of FIGS. 4A-4C, showing the moving armatures and the associated windings.
Figure 5B:
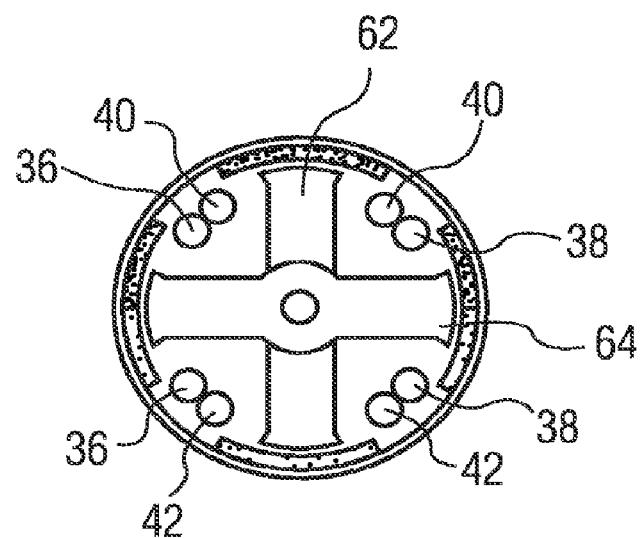
Figure 5C:
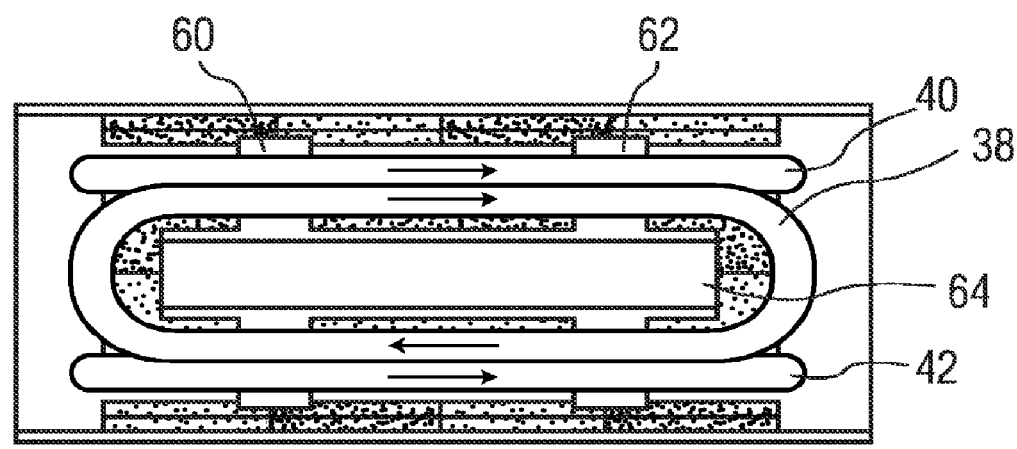
Figure 6A:
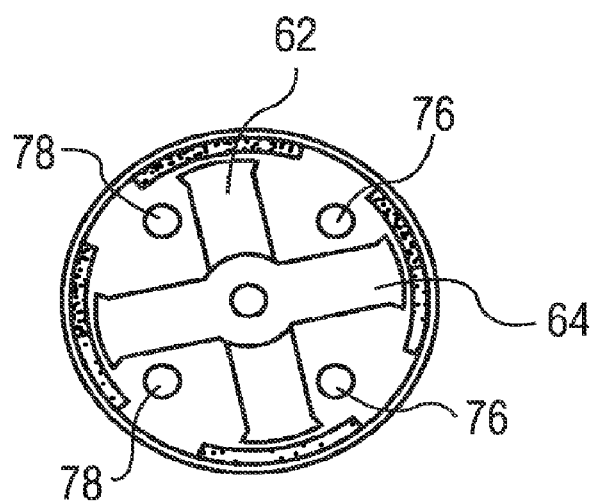
FIGS. 6A and 6B and 7A and 7B are cross-sectional views of a variation of the embodiment of FIGS. 4A-4C and 5A-5C.
Figure 6B:
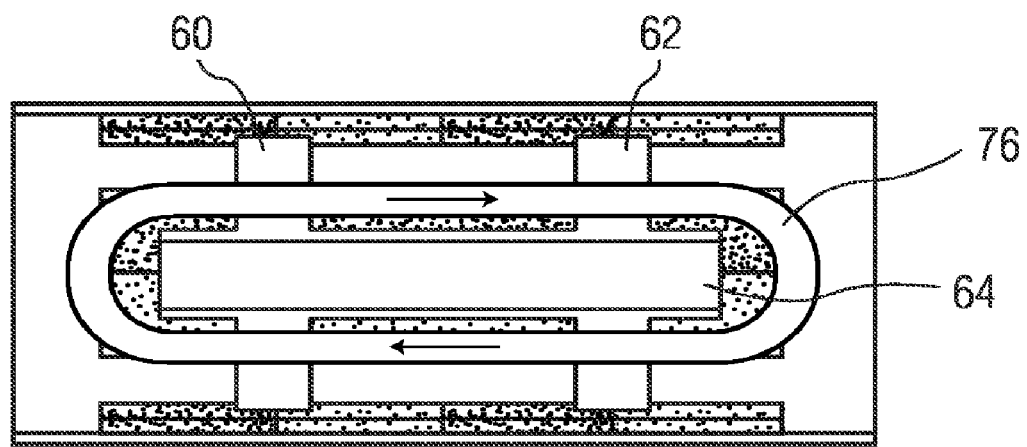
Figure 7A:
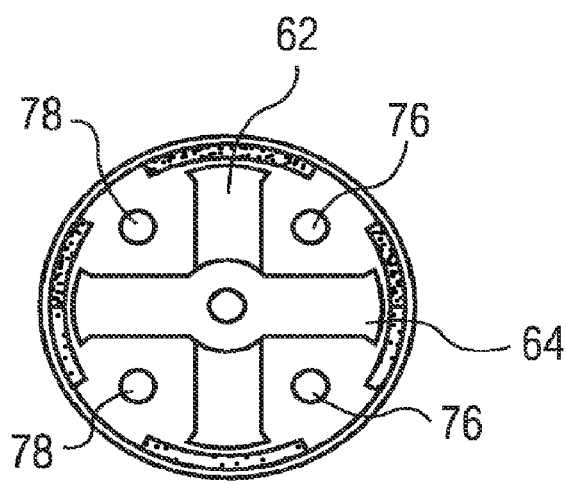
Figure 7B:
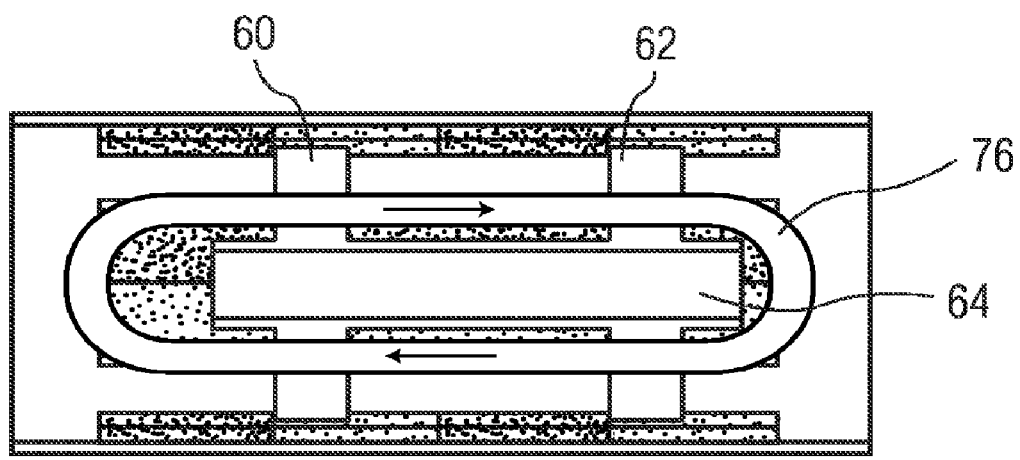

FIGS. 4A-4C and 5A-5C show an alternative arrangement which includes two spaced axial actuators/armatures 60 and 62 and a single tangential actuator/armature 64 (FIGS. 5A-5C). The housing and the permanent magnet arrangement on the interior surface of the housing for the tangential actuation is the same as for the above-described embodiment of FIGS. 2A-2C and 3A-3B. The permanent magnet arrangement for each axial actuator includes four successive magnet portions 70-73 for magnet arrangement 74, while magnet portions 70A-73A are for magnet arrangement 75. The magnet portions 70-73 and 70A-73A are all of equal length and alternate between north and south polarity. The two axial actuators 60 and 62 are positioned so that at rest they are positioned where adjacent north and south polarity portions abut, as shown most clearly in FIGS. 5A and 5C. This dual axial actuation is referred to as a "split tooth" arrangement. More magnet portions with axial actuators can be used, providing a stronger actuation in the axial direction. The winding arrangements (36, 38, 40 and 42) for the split tooth actuator are the same as for that discussed above for FIGS. 5B and 5C.

The four-winding embodiment can be driven by two full bridge circuits, one for the tangential windings (two partial windings) and one for the axial (also two partial windings).

The embodiment of FIGS. 6A-6B and 7A-7B is identical to the previous embodiment (FIGS. 4A-4C and 5A-5C), except that only two undivided windings are necessary. Windings 76 and 78 are provided as shown. Tangential actuation (FIGS. 6A-6B) will occur if the currents through the windings are in the same direction, while axial actuation (FIGS. 7A-7B) occurs if the currents are in the opposing direction. If the currents have different frequencies, a combined, complex movement of the spindle will occur.

The rotary/axial motion embodiments described above make use of a variety of materials. In these multiple degree of freedom arrangements, energy absorption/consumption due to friction in the bearing surfaces can become an important issue. While the energy supply (battery) remains constant, the consumption of energy will typically increase. To partially overcome this problem, the bearing elements which support the spindle within the housing in the various embodiments described above can be made of elastic material, which is typically characterized by very low internal damping properties. The use of elastic material of one kind or another will operate to reduce energy consumption due to bearing friction within a toothbrush or other personal care appliance.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A drive system for a personal care appliance, comprising:
    a housing;
    a first opposing pair of permanent magnets positioned longitudinally along an interior surface of the housing, each first permanent magnet having a first portion with a north polarity and a second portion with a south polarity, the first and second portions each extending the length of the first permanent magnet;
    a second opposing pair of permanent magnets, generally orthogonal with the first pair of permanent magnets, positioned longitudinally along the internal surface of the housing, each second permanent magnet having a plurality of parts along the length thereof, alternating between north and south polarities, the first part of one second permanent magnet having a north polarity and the first part of the other second permanent magnet having a south polarity;
    a first moving armature mounted within the housing for moving rotationally, when energized, the first armature extending longitudinally of the housing; and/or
    a second moving armature mounted within the housing for moving axially when energized;
    at least one drive winding positioned around at least one of the moving armatures;
    a spindle element to which the first and/or second armatures are connected or form a part of, the spindle element extending outwardly from one end of the housing and adapted to be connected to an output assembly which includes a workpiece, wherein the spindle rotates when the first armature rotates and moves axially when the second armature moves axially;
    a source of power; and
    programmable control means for applying the power to the drive winding in a selected manner to produce rotational and/or axial movement of the workpiece on the output assembly.

2. The drive system of claim 1, wherein at least one of the first and second armatures has two parts, one on each side of the spindle, and wherein the windings extend around both parts of the armature.

3. The drive system of claim 1, wherein the second armature has free ends which are substantially in registry with the width of the corresponding permanent magnets.

4. The drive system of claim 1, wherein the second pair of permanent magnets each include two parts of equal length.

5. A drive system for a personal care appliance, comprising:
    a housing;
    a first opposing pair of permanent magnets positioned longitudinally along an interior surface of the housing, each first permanent magnet having a first portion with a north polarity and a second portion with a south polarity, the first and second portions each extending the length of the first permanent magnet;
    a second opposing pair of permanent magnets, generally orthogonal with the first pair of permanent magnets, positioned longitudinally along the internal surface of the housing, each second permanent magnet having a plurality of parts along the length thereof, alternating between north and south polarities, the first part of one second permanent magnet having a north polarity and the first part of the other second permanent magnet having a south polarity;
    at least one moving armature mounted within the housing for moving rotationally or axially when energized;
    at least one drive winding positioned within the housing;
    a spindle element to which the at least one armature is connected or forms a part of, the spindle element extending outwardly from one end of the housing and adapted to be connected to an output assembly, which includes a workpiece, wherein the spindle rotates or moves axially, respectively, when the at least one armature rotates or moves axially;
    a source of power; and
    programmable control means for applying the power to the drive winding in a selected manner to produce rotational or axial movement of the workpiece on the output assembly.

6. The drive system of claim 5, wherein the at least one armature has two parts, one on each side of the spindle, and wherein the winding extends around the armature.

7. A drive assembly for a personal care appliance, comprising:

a housing;

first and second opposing pairs of spaced permanent magnet assemblies extending longitudinally of the housing, wherein each of the first pair of permanent magnet assemblies comprise north and south pole magnet sections which extend the length of the permanent magnet assemblies, and wherein the second pair of permanent magnet assemblies are positioned generally orthogonal to the first pair of permanent magnet assemblies, each of the second pair of permanent magnet assemblies having a plurality of parts along the length thereof, alternating between north and south polarities, the first part of one of the second pair of permanent magnet assemblies having a north polarity and the first part of the other of the second pair of permanent magnet assemblies having a south polarity;

a spindle member mounted within the housing and capable of moving rotationally and longitudinally;

first and second armature arrangements attached to or forming a part of the spindle element, wherein the first armature arrangement, when energized, moves the spindle member rotationally, while the second armature arrangement, when energized, moves the spindle element longitudinally;

a source of power; and a control assembly for selectively energizing the first and/or second armature assemblies to produce movement of the spindle element and a workpiece attached thereto.

* * * * *